United States Patent
Wuenn et al.

(10) Patent No.: US 9,017,997 B2
(45) Date of Patent: Apr. 28, 2015

(54) BIOREACTOR

(75) Inventors: Eberhard Wuenn, Goettingen (DE); Gerhard Greller, Goettingen (DE); Thorsten Adams, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 513 days.

(21) Appl. No.: 12/933,521

(22) PCT Filed: Mar. 13, 2009

(86) PCT No.: PCT/EP2009/001828
§ 371 (c)(1),
(2), (4) Date: Sep. 20, 2010

(87) PCT Pub. No.: WO2009/115241
PCT Pub. Date: Sep. 24, 2009

(65) Prior Publication Data
US 2011/0020922 A1    Jan. 27, 2011

(30) Foreign Application Priority Data
Mar. 20, 2008    (DE) .................. 10 2008 015 386

(51) Int. Cl.
C12M 1/12      (2006.01)
C12M 1/00      (2006.01)
C12M 3/06      (2006.01)

(52) U.S. Cl.
CPC .............. *C12M 29/04* (2013.01); *C12M 23/14* (2013.01); *C12M 23/34* (2013.01); *C12M 27/16* (2013.01)

(58) Field of Classification Search
CPC ...... C12M 23/14; C12M 23/34; C12M 27/16; C12M 29/04

USPC .......... 435/297.1–297.3, 286.1, 289.1, 303.1, 435/291.7

See application file for complete search history.

(56) References Cited

U.S. PATENT DOCUMENTS

| | | | |
|---|---|---|---|
| 4,535,062 A | | 8/1985 | Muller |
| 4,845,132 A | * | 7/1989 | Masuoka et al. ................ 521/53 |
| 4,943,535 A | | 7/1990 | Thompson et al. |
| 5,071,760 A | * | 12/1991 | Watanabe et al. ............. 435/394 |
| 6,544,788 B2 | | 4/2003 | Singh |
| 2002/0104631 A1 | * | 8/2002 | Hansen et al. ................ 162/125 |
| 2004/0159616 A1 | | 8/2004 | Cohee et al. |
| 2007/0000288 A1 | * | 1/2007 | Giro Amigo .................... 66/195 |
| 2008/0274536 A1 | * | 11/2008 | Hatano et al. ................. 435/243 |
| 2009/0027997 A1 | | 1/2009 | Meier |

FOREIGN PATENT DOCUMENTS

DE    19817081 A1    10/1999

OTHER PUBLICATIONS

International Preliminary Report on Patentability.

* cited by examiner

*Primary Examiner* — Michael Marcheschi
*Assistant Examiner* — Shanta G Doe
(74) *Attorney, Agent, or Firm* — Gerald E. Hespos; Michael J. Porco; Matthew T. Hespos

(57) ABSTRACT

The invention relates to a bioreactor for cultivating cells having a filter bag for separating culture fluid and cells, the filter medium of the filter bag having a degree of swelling of less than 1%. The bioreactor according to the invention is characterized by a high durability of the filter bag thereof.

15 Claims, 3 Drawing Sheets

BIOREACTOR

BACKGROUND OF THE INVENTION

1. Field of the Invention

The invention relates to a bioreactor for culturing microorganisms and cells.

2. Description of the Related Art

In order to culture microorganisms or cells of animal or plant origin in a bioreactor in high density, it is frequently necessary to keep the concentration of toxic metabolic products such as ammonium or lactate in the culture medium as low as possible. This is achieved by continuously removing cell-free polluted medium from the bioreactor and replacing it by fresh culture medium. The separation of cells and culture medium can be achieved, for example, by centrifugation or filtration. The operation of discharge and replacement with an equal volume of culture medium is designated perfusion. The perfusion step can proceed outside the bioreactor, but this is complex in terms of apparatus and is associated with a high risk of contamination. In the case of bioreactors having flexible walls, cell-free culture medium can be taken off in a very simple manner by mounting a perfusion filter on the inner wall of the reactor.

A disposable perfusion bioreactor of this type is marketed by Sartorius Stedim Biotech GmbH under the name CultiBag® RM. Mixing proceeds here by means of a tilting device which makes the culture medium run constantly to and fro in the flat bag. The cell-free culture medium is separated off via a filtration module in the form of a filter bag consisting of a large-pored filter medium the periphery of which is welded to one of the inner bioreactor walls.

The necessity of selecting a filter medium which is impermeable to cells and readily permeable to other components of the cell suspension limits the effective pore size of the filter layer to a maximum of 10 µm. Suitable filters are microfiltration membranes which are known to have a narrow pore size distribution with a large void volume. A disadvantage of the materials previously used as perfusion membrane in the bags is their inadequate mechanical strength for long-term use.

Disadvantages of this bioreactor result, in addition, from the circumstance that in the case of the filter medium, warping and creasing of the filter medium occurs which, in relatively long-term operation, leads to breaking of the filter medium owing to the mechanical stress in the crease regions which is caused by the movement of the culture medium.

U.S. Pat. No. 6,544,788 B2 discloses a bioreactor having flexible walls which, for the purpose of perfusion, has a filter module floating on the surface of the culture medium. The mechanically stable floating body, however, is of limited use if a reduced culture volume is employed in the starting phase of a cell culture. Then, the float housing can impact onto the bag wall and damage same. In addition, the filter surface areas required for the perfusion are so large that exchange of gases, in particular oxygen, with the culture medium is impaired.

The object of the present invention is therefore to propose a bioreactor having a filter module suitable for perfusion, which filter module is distinguished by a high mechanical stability in long-term use and does not hinder exchange of gases with the culture medium.

SUMMARY OF THE INVENTION

The object of the invention is achieved by a bioreactor having at least one filter bag, which is fixed to the liquid-wetted inner surface of a wall of the bioreactor and in its interior has a collecting and/or distributing compartment which is in communicating connection by means of at least one connection for supply and/or removal of media, wherein at least one filter bag wall is formed at least in part by a hydrophilic filter medium. Surprisingly, it has been found that even in the case of a filter bag which covers an entire wall of the bioreactor, crease formation of the filter medium is avoided when the filter medium in water has a degree of swelling and/or shrinkage of at most 1%.

The degree of swelling of the filter medium is determined as follows:

From one section of a filter medium which was dried to constant weight at room temperature in ambient air, a circular piece of defined diameter is stamped out, labeled and incubated at RT in RO water (RO=Reverse Osmosis). After 24 h, the sample is laid free of creases on a pore-free smooth surface and the diameter determined in the web direction and transverse to the web direction. From the ratio of the diameter of the sample stored in water to the original diameter, the percentage degree of swelling is calculated. The degree of shrinkage is determined similarly by measuring a sample incubated in RO water. After drying for 24 h to constant weight at RT, the diameter is measured again and the degree of shrinkage calculated.

By virtue of the filter bag being fixed to the inner surface of a wall of the bioreactor and not floating on the surface of the culture medium, the gas exchange between gas phase and culture medium is not impaired. Owing to the overpressure prevailing in the bioreactor, or by applying a reduced pressure in the filter bag, the culture medium is transported into the filter bag through the hydrophilic filter medium, wherein the collecting and/or distributing compartment in the interior of the filter bag acts as a collecting compartment for the filtered culture medium which can be removed from the bioreactor via a connection.

Hydrophilic filter media are taken to mean those in which an RO water droplet of 10 µl which is applied unpressurized to a dried filter medium is absorbed completely by the porous matrix of the filter medium in the course of 600 seconds at RT in static ambient air.

Preferably, the bioreactor is constructed in such a manner that the wall of the bioreactor forms one of the filter bag walls. In further embodiments, the filter bag is fixed via spacers to the inner wall of the bioreactor or a plurality of filter bags are constructed as a filter bag stack which are separated by open channels situated between the filter bags. By means of both measures, the filter surface area available for filtration is enlarged further which contributes to a considerable improvement of perfusion, in that blocking of the filter medium is avoided.

In a further preferred embodiment of the invention, at least one filter bag wall consists at least in part of a hydrophobic filter medium. The head space above the culture medium can be charged with gas. Thus, for example, during an interruption of the filtration, gas can be introduced into the bioreactor via an at least partly hydrophobic filter bag. The collecting and/or distributing compartment of the filter bag acts here as a distributing compartment for the gas. The gas introduced is preferably nitrogen, air or oxygen. The collecting and/or distributing compartment of the filter bag can also be subdivided fluid-tightly in such a manner that the hydrophilic filter medium adjoins the collecting compartment and the hydrophobic filter medium adjoins the distributing compartment. In this embodiment, culture medium can be removed and gas supplied simultaneously via the filter bag, wherein two separate connections are present in each case for supplying and removing the media.

The hydrophilic filter medium consists of a membrane filter (hereinafter designated membrane), of a filter layer (woven fabric, nonwoven) made up of fibers, or of a layer sintered from particles. Such hydrophilic filter media consist of natural or synthetic polymers and also of inorganic materials, wherein the hydrophilicity can be produced or reinforced by measures of modifying the polymers or filter media which are familiar to those skilled in the art. Preferred polymeric materials for producing hydrophilic filter media are aliphatic polyamides, polysulfones and polyethersulfones, polyesters, polyvinylidene halides, acrylic polymers, acrylic copolymers and cellulose esters.

Hydrophobic filter media consist of natural or synthetic polymers and also of inorganic materials, wherein the hydrophobicity can be produced or reinforced by measures of modifying the polymers or filter media which are familiar to those skilled in the art. Preferred polymeric materials for producing hydrophobic filter media are polyalkenes, halogenated polyalkenes, polysulfones and polyethersulfones, aliphatic polyamides, polyesters, acrylic polymers, acrylic copolymers and cellulose esters.

In a preferred embodiment of the invention the hydrophilic and/or hydrophobic filter medium is microporous. Microporous is taken to mean a pore size range of 0.1 to 20 µm. The hydrophilic filter medium is preferably used in a pore size between 0.1 and 10 µm and the hydrophobic filter medium is preferably used in a pore size within a range of 0.1 to 0.8 µm.

In a further preferred embodiment of the invention, the filter medium consists of a membrane which, on at least one side which faces the collecting and/or distributing compartment of the filter bag, is connected to a porous fabric made of thermoplastic polymer fibers which do not swell or swell only minimally on contact with the aqueous culture medium. The porous fabric consists of a nonwoven, woven fabric, knitted fabric or mesh, wherein a nonwoven made of polymer fibers is preferred. Such mechanically reinforced, microporous, hydrophilic or hydrophobic membranes, on contact with the culture medium, have no or only minimal swelling (<1%) and are therefore particularly suitable as filter medium.

The connection can be produced by laminating the membrane to the fabric under the action of pressure and elevated temperature, or carried out as an integral connection in which the membrane material has penetrated in part or completely into the fabric. The latter is effected during the membrane production process.

In this manner an unreinforced hydrophilic polyamide membrane (nylon 6,6), on wetting with water, has a swelling of approximately 2%. If a nylon 6,6 membrane is reinforced with a 12 g/m² polyester nonwoven, the swelling on wetting with water is only 0.4%. A microporous nylon 6,6 membrane, which is reinforced on one side by laminating to a polyethylene/polypropylene nonwoven, has only a changing dimension in water of less than 0.35%. Filter bags fabricated therefrom, even after use for 7 days in a bioreactor, exhibited no warping or creasing.

Preferably, the thermoplastic polymer fibers are hydrophobic. Owing to the hydrophobic properties, the porous fabric is a first hydrophobic barrier to the culture medium. This first hydrophobic barrier to the culture medium is preferably not overcome until beyond a pressure difference of 20 mbar for perfusion. The hydrophobic barrier prevents the culture medium from penetrating into the interior of the filter bag, for example during the multiplication or start phase, and is no longer available to the bioreactor as culture medium during this time and at times where culture medium is not intended to be removed.

For increasing the hydrophobic action, those skilled in the art can use familiar measures of modification. The choice of a compacted nonwoven material produced from relatively thin fibers as a porous fabric is also possible.

Furthermore, it has proven particularly useful to connect the membrane on both sides to a porous fabric made of thermoplastic polymer fibers, for example a polyethersulfone membrane which is reinforced on two sides by a polyethylene/polypropylene nonwoven exhibits in water a degree of swelling of only 0-0.2% and is particularly well suited for use as a filter bag wall in bioreactors.

When hydrophobic polymer fibers are used, the porous fabric which does not adjoin the collecting and/or distributing compartment of the filter bag is not only a second hydrophobic barrier to the culture medium, but also forms an effective mechanical surface protection for the membrane. This second hydrophobic barrier is made so as to be able to be overcome by the culture medium preferably starting from a pressure difference of 1 mbar. The two-sided reinforcement of the microporous membrane filter also improves, furthermore, the planar properties of the laminated filter medium and facilitates processing during the production of the filter bag for the bioreactor.

Alternatively, the membrane, for use as a filter bag wall, can also be reinforced integrally by the porous fabric such as, e.g., in the case of a cellulose acetate membrane which, unreinforced, exhibits on contact with water a swelling of 0.7-1.36, but integrally reinforced with polypropylene nonwoven exhibits in water a degree of swelling of only 0.1-0.26. Or such as in the case of a polyamide membrane (nylon 6,6) which, integrally reinforced with a polyester woven fabric likewise exhibits a swelling of 0.1-0.20.

Preferably, the porous fabric and the inner surface of the wall of the bioreactor to which the filter bag is fixed consist of polymer materials which are selected from the same group of chemical substances. This achieves a particularly durable and mechanically stable connection during production by melting the polymer materials of the bioreactor wall and of the porous fabric.

A porous fabric, the polymer fibers of which consist of core-sheath fibers in which the core consists of a more thermally stable polymer than the sheath polymer, has proven particularly useful. Joining the microporous filter medium to porous fabrics swelling or shrinking correspondingly little, further decreases the degree of swelling and/or shrinkage of the filter medium.

A particularly durable, fluid-tight connection of the at least one filter bag to the inner surface of the wall of the bioreactor is achieved when the filter medium in its peripheral circumferential region is fixed to the inner surface of the wall of the bioreactor by welding, in particular when at least one of the walls of the bioreactor is constructed as a flexible wall.

A particularly advantageous filter bag is a filter bag which is constructed so as to be flexible. It is possible thereby to dispatch the complete bioreactor having flexible walls, after sterilization, to the consumer packaged ready for use and occupying a small volume. The bioreactor according to the invention is constructed so as to be sterilizable by heat, steam, radiation or gas. Since the filter bag is flexible, it adopts the shape of a chicane as soon as the bioreactor with flexible walls is accommodated by a support container forming outer chicanes. This leads to an improved mixing of the culture medium and an associated increased performance of the bioreactor.

In a further embodiment of the invention, the filter medium, for special applications in which substances are to be obtained in a targeted manner, consists of ultrafiltration materials having exclusion (cutoff) limits in the range between about 500 and about 1 million daltons.

In the event that certain substances, for example toxic substances or viruses, must not pass into the perfusate during the perfusion, the filter medium consists of membrane adsorbers. Membrane adsorbers are taken to mean ion-exchange membranes, adsorption membranes or active membranes, in particular biologically active membranes. In a further preferred embodiment of the invention, the filter bag includes a spacer in its collecting and/or distributing compartment. It has proved to be expedient for construction if the connection for the supply and/or removal of media is conducted through the wall of the bioreactor.

The bioreactor according to the invention, in a further embodiment, has a mixing device by which the culture medium is mixed. Preference is given to mixing devices which are constructed as tilting, see-sawing, oscillating, vibrating, shaking, gas-introducing, stirring, transfer pump and/or pneumatic devices.

The invention will be described in more detail by means of the figures hereinafter and an exemplary embodiment.

DETAILED DESCRIPTION OF THE PREFERRED EMBODIMENT

Figure 1A:
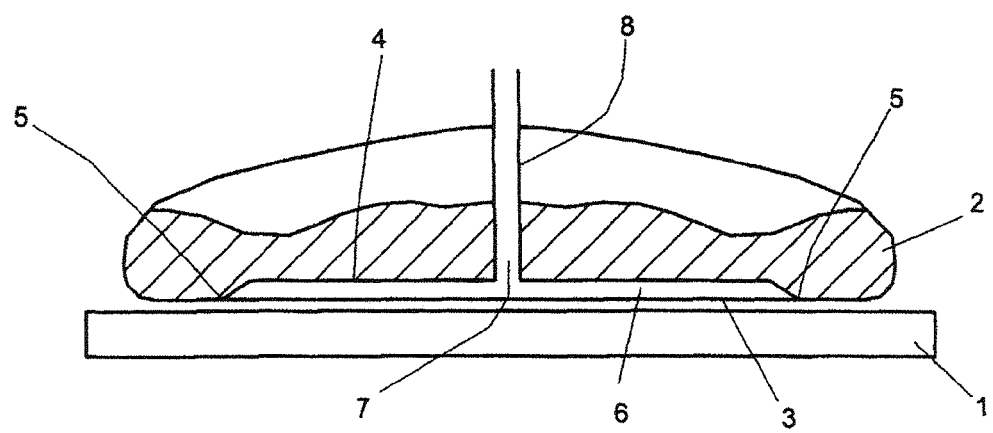
FIG. 1 shows a diagrammatic view of a bioreactor according to the invention having a filter bag.
Figure 1B:
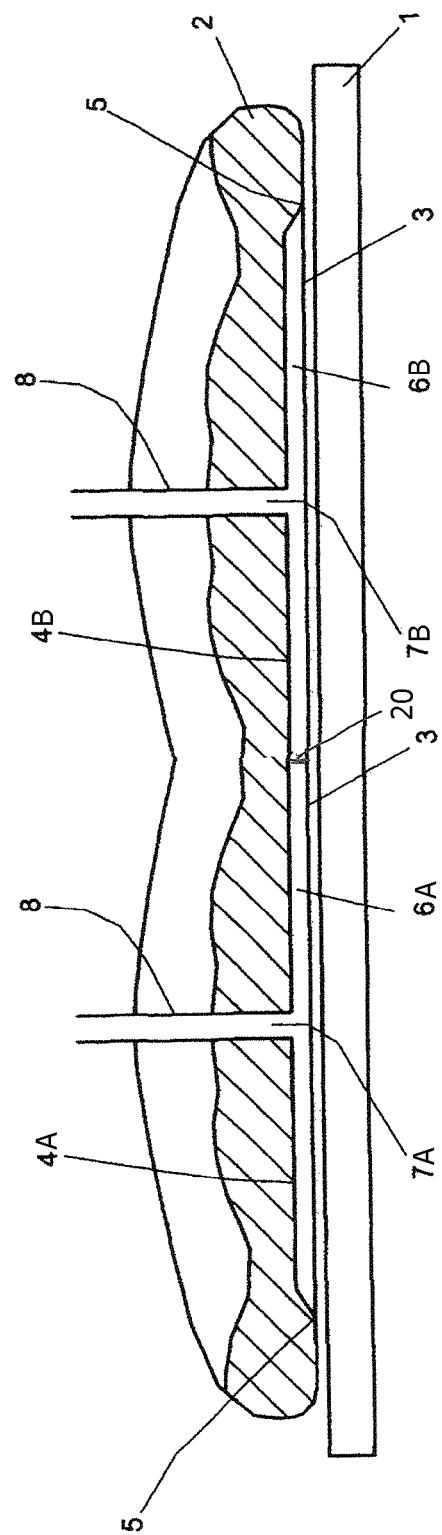

According to FIG. 1A, the bioreactor lies on a mixing device 1, by the motion of which the culture medium 2 is mixed. On the inner surface of the bottom wall 3 of the bioreactor, a filter medium 4 is fixed 5 in its periphery to the bioreactor wall. The wall of the bioreactor 3 and the filter medium 4 delimits a collecting/distributing compartment 6 which at one point is pierced by a connection 7 and via which by means of a flexible tube 8 media can be supplied or removed to or from the collecting/distributing compartment.

Figure 2:
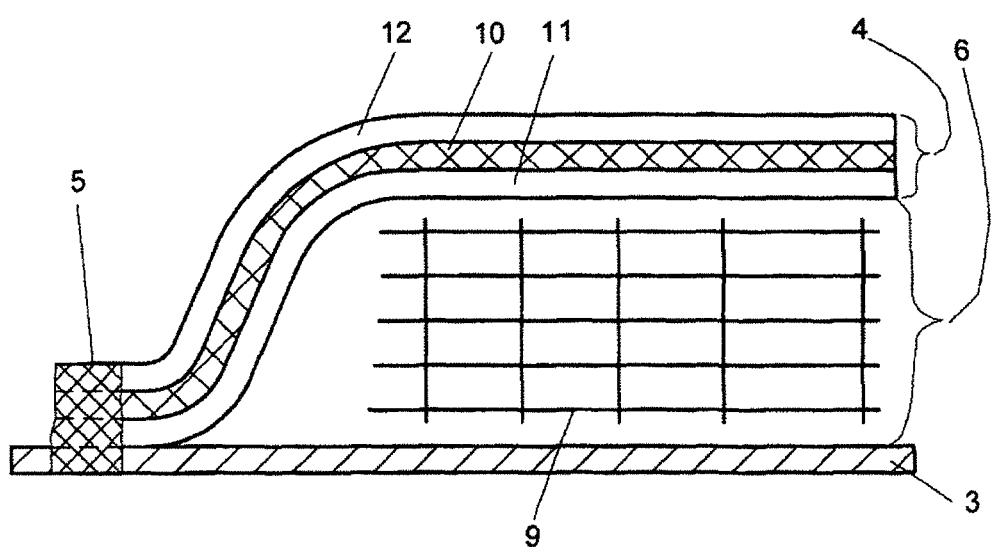
FIG. 2 shows a more detailed structure of a filter bag.

According to FIG. 2, a filter bag is formed from the wall of the bioreactor 3 and the filter medium 4. In the collecting compartment and distributing compartment 6 there is situated a spacer 9 which prevents the collapse of the collecting/distributing compartment. The filter medium 4 is fixed 5 in its periphery to the wall of the bioreactor 3. The filter medium 4 consists of a membrane 10 which is connected to a porous fabric 11 on the side facing away from the interior of the bioreactor. As a further embodiment, the membrane, in addition, is also connected to a porous fabric 12 on the side facing the interior of the bioreactor.

Exemplary Embodiment

A 10 liter bioreactor Cultibag RM® constructed as a pouch having an integrated perfusion membrane is clamped on a tilting platform heated to 37° C. and connected to a BIOSTAT® control unit. For this purpose the top side of the pouch is provided with a multiplicity of passages which serve for charging, gas exchange, connection of the light conductors for pH and oxygen sensors dipping loose into the culture compartment at flexible tube ends, sampling and also removal of the perfusate.

The bioreactor is equipped with a filter bag welded to the middle wall thereof, the filter medium which does not swell on wetting of which filter bag consists completely of a hydrophilic polyethersulfone membrane (pore size 1.2 μm) which is connected by adhesion on one side to a stable polypropylene/polyethylene core-shell nonwoven (100 g/m$^2$). A flexible tubing fitting (4 mm internal radius) is welded into the filter medium in such a manner that in the culture compartment of the pouch a flexible tubing connection can be produced by means of a double fitting provided in the opposite pouch wall through which removal of the perfusate to the outside is possible.

The reinforced filter medium having the dimensions 25×40 cm is connected fluid-tightly by the nonwoven side via a 5 mm wide welded seam internally to the polyethylene layer, facing the culture medium, of the three-layer inner film of the reactor pouch. As spacer between inner film and filter medium, an industrial textile (thickness 0.6 mm) cut to 23×38 cm is placed into the filter bag.

Chinese hamster ovary (CHO) cells of a preculture (3×10$^6$ cells/ml) are diluted with ProCH05 medium to 2.5 liters of cell suspension of a cell density of 5×10$^5$ and transferred under sterile conditions at 37° C. to the liter bioreactor. Mixed with 16 tilting motions ("rocking rate") per minute, the cell reproduction starts after addition of nutrient medium under a 6 mbar gas cushion, constant oxygen content and constant pH. By daily sampling, the cell reproduction is followed up to the target concentration of 3×10$^6$/ml. After charging to 5 liters end volume and at 20 tilting motions per minute, the perfusion of the cell culture starts at an exchange rate of 3.5 ml/min (5 l/d) through the integrated membrane. Samples of the perfusate are tested routinely during the 7-day perfusion for ammonium, lactate and cell content.

During the entire culture time period, the filtration medium is washed over in the cycle of the tilting motion and touched by the loose internals of the bioreactor. Damage of the filter medium caused thereby or detaching or tearing of the membrane layer at the connection surfaces to the inner wall of the bioreactor would immediately cause a high cell concentration of the perfusate.

Result: During the perfusion, no cells could be found in the perfusate. The filter medium during the culture lay flat, free from creases, on the filter bag. For confirmation of the integrity of the hydrophilic filter medium and the stability of the filter bag, the filter bag was subjected to a "back pressure" test in which the filter bag is inflated in the fluid-filled bioreactor. Up to 90 mbar back pressure, no air bubbles could be seen. Isolated bubble traces in the vicinity of the seal rim (region of greatest expansion) were not see until the pressure was increased.

The invention claimed is:

1. A bioreactor comprising: at least one wall having opposite inner and outer surfaces and defining an interior of the bioreactor for holding a culture medium, a reinforced hydrophilic filter medium having a peripheral edge fixed to the inner surface of the at least one wall of the bioreactor, all areas of the reinforced hydrophilic filter medium inward of the peripheral edge being unconnected to the at least one wall of the bioreactor to define a collection/distributing compartment between the inner surface of the at least one wall of the bioreactor and the reinforced hydrophilic filter medium inward of the peripheral edge thereof, the reinforced hydrophilic filter medium comprises a hydrophilic microporous filter membrane having a first surface facing toward the collection/distributing compartment and a second surface facing toward the interior of the bioreactor, the reinforced hydrophilic filter medium further having a porous reinforcing fabric connected to each of the first and second surfaces, so that the hydrophilic microporous filter membrane is reinforced by the porous reinforcing fabric connected thereto and has a degree of swelling and/or shrinkage of at most 1% in water; and at least one connection extending from the collecting/distributing compartment to areas outside the bioreactor for supply or removal of media.

2. The bioreactor as claimed in claim 1, further comprising at least one spacer disposed between the filter medium and the inner surface of the at least one wall of the bioreactor to prevent collapse of the collecting/distributing compartment.

3. The bioreactor as claimed in claim 1, wherein the porous reinforcing fabric is formed at least in part a hydrophobic fibers.

4. The bioreactor as claimed in claim 1, wherein the porous reinforcing fabric is made of thermoplastic polymer fibers.

5. A bioreactor having at least one filter bag fixed to an inner surface of a wall of the bioreactor and having an interior defining a collecting/distributing compartment which is in communicating connection by at least one connection for supply or removal of culture medium, the at least one filter bag having a first wall formed by the inner surface of the wall of the bioreactor and at least one second wall formed at least in part by a hydrophilic filter medium, the filter medium having a degree of swelling and/or shrinkage of at most 1% in water, wherein the filter medium comprises a membrane which, on at least one side that faces the collecting/distributing compartment of the at least one filter bag, is connected to a porous fabric made of thermoplastic polymer fibers, wherein the porous fabric is hydrophobic and is a hydrophobic barrier to the culture medium which can be overcome starting at a pressure difference of 20 mbar.

6. A bioreactor having at least one filter bag fixed to an inner surface of a wall of the bioreactor and having an interior defining a collecting/distributing compartment which is in communicating connection by at least one connection for supply or removal of culture medium, the at least one filter bag having a first wall formed by the inner surface of the wall of the bioreactor and at least one second wall formed at least in part by a hydrophilic filter medium, the filter medium having a degree of swelling and/or shrinkage of at most 1% in water, wherein the filter medium comprises a membrane, and wherein the membrane is connected on both sides to a porous fabric made of thermoplastic polymer fibers and wherein the porous fabric which does not adjoin the collecting and/or distributing compartment of the at least one filter bag is a hydrophobic barrier to the culture medium which can be overcome starting at a pressure difference of 1 mbar.

7. The bioreactor as claimed in claim 4, wherein the porous reinforcing fabric and the inner surface of the at least one wall of the bioreactor are made of materials selected from the same group of chemical substances.

8. The bioreactor as claimed in claim 4, wherein the reinforced hydrophilic filter medium is fixed to the inner surface of the at least one wall of the bioreactor via the porous reinforcing fabric.

9. The bioreactor as claimed in claim 1, wherein the at least one wall of the bioreactor is flexible.

10. The bioreactor as claimed in claim 9, wherein the reinforced hydrophilic filter medium is flexible.

11. The bioreactor as claimed in claim 1, wherein the hydrophilic filter medium has exclusion limits in the range between about 500 and about 1 million daltons.

12. The bioreactor as claimed in claim 1, wherein the hydrophilic filter medium is a membrane adsorber.

13. The bioreactor as claimed in claim 1, wherein the porous reinforcing fabric is a polypropylene nonwoven.

14. The bioreactor as claimed in claim 13, wherein the porous reinforcing fabric is a laminated on each of the first and second surfaces of the hydrophilic microporous filter membrane.

15. A disposable perfusion bioreactor having at least one flexible wall and at least one flexible filter bag fixed to an inner surface of the at least one flexible wall of the bioreactor, the at least one flexible filter bag having an interior defining a collecting/distributing compartment with at least one connection for supply or removal of media, the at least one flexible filter bag having a first wall formed by an area of the at least one flexible wall of the bioreactor and a second wall disposed in the bioreactor and having an outer periphery fixed to the at least one flexible wall of the bioreactor, the second wall being formed by a hydrophilic filter medium that comprises a hydrophilic microporous filter membrane and a reinforcement layer affixed laminated to a first surface and a second surface of the hydrophilic microporous filter membrane, so that the hydrophilic microporous filter membrane in water has a degree of swelling and/or shrinkage of at most 1%.

\* \* \* \* \*